(12) United States Patent
Duran et al.

(10) Patent No.: US 6,630,001 B2
(45) Date of Patent: *Oct. 7, 2003

(54) COMPLIANT DEHYRATED TISSUE FOR IMPLANTATION AND PROCESS OF MAKING THE SAME

(75) Inventors: Carlos M. G. Duran, Missoula, MT (US); David T. Cheung, Arcadia, CA (US); David C. Pang, Missoula, MT (US)

(73) Assignee: International Heart Institute of Montana Foundation, Missoula, MT (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/103,874

(22) Filed: Jun. 24, 1998

(65) Prior Publication Data

US 2001/0004715 A1 Jun. 21, 2001

(51) Int. Cl.⁷ .................................................. A61F 2/02
(52) U.S. Cl. .................................. 623/23.72; 623/11.11; 623/915; 623/917; 8/94.11
(58) Field of Search ............................... 623/2.13, 2.42, 623/915, 917, 918, 11, 11.11, 23.72; 8/94.11

(56) References Cited

U.S. PATENT DOCUMENTS

| | | | |
|---|---|---|---|
| 2,106,261 A | 1/1938 | Weidemann | |
| 2,610,625 A | 9/1952 | Sifferd et al. | |
| 2,645,618 A | 7/1953 | Ferrari, Jr. | |
| 2,659,986 A | 11/1953 | Hink, Jr. | |
| 3,257,279 A * | 6/1966 | Schain | 8/94.11 |
| 3,939,260 A | 2/1976 | Lafon | |
| 4,277,238 A | 7/1981 | Katagiri | |
| 4,280,954 A | 7/1981 | Yannas et al. | |
| 4,300,243 A | 11/1981 | Baumgartner | |
| 4,357,274 A | 11/1982 | Werner | |
| 4,383,832 A | 5/1983 | Fraefel et al. | |
| 4,578,067 A | 3/1986 | Cruz, Jr. | |
| 4,703,108 A | 10/1987 | Silver et al. | |
| 4,704,131 A | 11/1987 | Noishiki et al. | |
| 4,760,131 A | 7/1988 | Sundsmo et al. | |
| 4,801,299 A | 1/1989 | Brendel et al. | |
| 4,911,915 A | 3/1990 | Fredenburgh | |
| 5,028,597 A | 7/1991 | Kodama et al. | |
| 5,116,552 A | 5/1992 | Morita et al. | |
| 5,131,850 A | 7/1992 | Brockbank | |
| 5,336,616 A | 8/1994 | Livesey et al. | |
| 5,447,536 A * | 9/1995 | Girardot et al. | 8/94.11 |
| 5,476,516 A * | 12/1995 | Seifter et al. | 8/94.11 |
| 5,518,878 A | 5/1996 | Wilkins et al. | 435/1.3 |
| 5,674,290 A | 10/1997 | Li | |
| 5,746,775 A * | 5/1998 | Levy et al. | 8/94.11 |
| 5,931,969 A * | 8/1999 | Carpentier et al. | 8/94.11 |
| 2001/0000804 A1 * | 5/2001 | Goldsteiin et al. | 623/23.72 |

FOREIGN PATENT DOCUMENTS

| | | |
|---|---|---|
| GB | 0716161 | 9/1954 |
| WO | 98/07452 | 2/1998 |

* cited by examiner

Primary Examiner—Paul B. Prebilic
(74) Attorney, Agent, or Firm—Gabor L. Szekeres

(57) ABSTRACT

A process for preparing pliable soft tissue specimen which are resistant to cracking and devoid of viable cells includes the steps of treating native soft tissue obtained from a donor by a gradually increasing gradient of aliphatic alcohol or other suitable water miscible polar organic solvent until the last alcohol (or other solvent) solution has at least 25% by volume of the organic liquid. Thereafter, the tissue specimen is treated with a solution containing glycerol or low molecular weight (<1000 D) polyethylene glycol, and polyethylene glycol of a molecular weight between approximately 6,000 to 15,000 D and heparin. Thereafter, the tissue specimen is briefly immersed in aqueous heparin solution, frozen and lyophilized. The tissue specimen is suitable for implantation as a homograft or xenograft, with or without rehydration.

30 Claims, No Drawings

COMPLIANT DEHYRATED TISSUE FOR IMPLANTATION AND PROCESS OF MAKING THE SAME

BACKGROUND OF THE INVENTION

1. Field of the Invention

The present invention is in the field of implant materials. More particularly, the present invention is directed to compliant dehydrated implant materials which have no viable cells, and can be stored and transported without being immersed in liquid. The present invention is also directed to the process of producing said implant materials.

2. Brief Description of the Prior Art

The use of autografts, homografts and xenografts for augmenting or replacing defective tissues in humans and animals has been known for a long time. From the standpoint of providing suitable materials for implantation, augmenting or replacing hard tissues, such as bone, presents a different type of problem than augmenting or replacing soft tissues. In the selection of substitute materials for hard tissue graft, the strength and hardness of the graft are important whereas compliance and flexibility are, generally speaking, less crucial.

On the other hand, in the selection of soft tissue materials for implantation, compliance and flexibility of the graft material are usually of utmost importance because the soft tissue replacement material usually must closely match the healthy functional tissue that will be replaced. In this regard it must be remembered that natural soft tissue containing collagen is strong and able to withstand repeated three-dimensional stress as well as bending and deformation. Often natural soft tissue acts as a physical barrier that must maintain its structural integrity. Ideally, replacement or augmentation soft tissue that is utilized in implantation should have the same characteristics as the natural soft tissue that it replaces, and should be easy to obtain, store and transport. These, however are difficult goals that the prior art has been striving to attain, and up to the present invention only with moderate success.

More particularly, in accordance with one major approach in the prior art to preserve soft tissue for eventual implantation, tissues of human or animal origins have been treated with chemical modifiers/preservatives, such as glutaraldehyde, which cross-links collagen and other proteins. The glutaraldehyde treated tissues have been shown to be adequately resistant to mechanical fatigue as well as biodegradation when implanted in human patients. However, the glutaraldehyde cross-linking alters the viscoelastic properties of tissues, and therefore, as a result of host response undesirable calcification and build-up of peripheral granulation tissues usually occur in the implants with time. Glutaraldehyde is an effective biocidal (sterilyzing) agent, but when exposed to air it slowly loses its biocidal effectiveness. Therefore, the tissue intended for implantation (bioprosthesis) must be kept in glutaraldehyde solution during storage and transportation and the package including the glutaraldehyde soaked bioprosthesis must be kept tightly sealed. Moreover, it must not be exposed to significantly elevated temperature. Because of these requirements the costs of utilizing glutaraldehyde-treated soft tissue bioprostheses are high. Glutaraldehyde is toxic, and therefore it must be carefully removed from the bioprosthesis by rinsing before implantation. This represents still another disadvantage of glutaraldehyde-treated bioprostheses.

Another major approach for providing soft tissue bioprosthesis in the prior art utilizes liquid sterilants other than glutaraldehyde. Some of these alternative approaches also avoid the calcification problems associated with glutaraldehyde treated implants. However, in accordance with these processes also, to avoid brittleness and to more-or-less maintain the physical integrity of the bioprostheses the tissues have to be maintained, stored and transported in liquid media up to the time immediately preceding implantation.

Still another alternative method for providing soft tissue bioprostheses is the use of cryo-preserved fresh tissues of homograft (tissue from the same species). Because of recent advances in cryo-preservation, the cryo-preserved fresh tissues have recently made homograft implants relatively more successful and more accepted as an alternative to glutaraldehyde-preserved xenograft. A serious disadvantage of cryo-preserved bioprostheses is the difficulty to assure that they are free of infectious disease agents. The costs of preparing and handling of cryo-preserved bioprosthesis tissues is also very high because of the need for keeping the tissues at all times below the usual or normal freezer temperatures.

From among the numerous patent disclosures in the prior art directed to preparing and/or preserving biological tissue for implantation or other use as replacement tissue, U.S. Pat. Nos. 5,116,552 (Morita et al.) and 5,336,616 (Livesey et al.) are mentioned as of interest to the present invention. U.S. Pat. No. 5,116,552 (Morita et al.) describes a process for preparing lyophilized collagen sponge for medical applications, such as artificial skin. The process of this reference comprises the steps of impregnating cross-linked collagen sponge with an aqueous solution of a hydrophilic organic solvent, freezing the sponge and thereafter vacuum drying (lyophilizing) it. However, the resulting freeze-dried product is not pliable and is not protected from cracking because the water and the hydrophilic solvent or solvents have been removed in the lyophilization step. U.S. Pat. No. 5,336,616 (Livesey et al.) describes treatment of soft tissue obtained from a source, such as a cadaver, with solutions containing antioxidants, protease inhibitors and antibiotics (stabilizing solution), with enzymes and detergents to remove viable antigenic cells (processing solution), and after decellularization with a cryopreservative solution that prevents destructive ice crystal formation while the tissue is frozen. The cryo-preserving solution may include a combination of organic solvent and water. After lyophilization the product is stored and transported in a sealed container in an inert gas atmosphere, thus protected from atmospheric moisture. Prior to implantation the tissue is rehydrated and must be restored with immunotolerable viable cells to produce a permanently acceptable graft for implantation.

Still other disclosures pertaining to the preparation and/or preservation of biological tissue for implantation, or related subjects, can be found in U.S. Pat. Nos. 2,106,261; 2,610,625; 2,645,618; 3,939,260; 4,277,238; 4,280,954; 4,300,243; 4,383,832; 4,578,067; 4,703,108; 4,704,131; 4,760,131; 4,801,299; 4,911,915; 5,028,597; 5,131,850; 5,674,290 and U.K. Patent Specification 716,161.

SUMMARY OF THE INVENTION

It is an object of the present invention to provide a soft tissue graft suitable for implantation in humans or other mammals which graft after rehydration has substantially the same mechanical properties as the natural soft tissue from which the graft was obtained.

It is another object of the present invention to provide a soft tissue graft that satisfies the foregoing objective, that is also devoid of viable cells and does not require inoculation with viable cells prior to implantation.

It is still another object of the present invention to provide a soft tissue graft that satisfies the foregoing objectives, that can be stored and transported in a dehydrated form.

The foregoing and other objects and advantages are attained by a soft tissue preparation that in its dehydrated state is compliant, resists cracking, is devoid of viable cells and which is obtained by successively treating natural soft tissue:

with liquid compositions of gradually increasing concentrations of a $C_1$–$C_3$ alcohol, or other polar water miscible organic solvent in water, until the last of said liquid compositions contains at least approximately 25% by volume alcohol, or the other organic solvent, or mixtures thereof, the balance being water;

thereafter with a second liquid composition of aqueous glycerol or of low molecular weight (<1000 D) polyethylene glycol, containing the glycerol or the low molecular weight polyethylene glycol, or mixtures thereof, in a concentration range of approximately 10 to 50% by volume, said second liquid composition also containing approximately 3–20% weight by volume polyethylene glycol of a molecular weight in the range of 6,000 D to 15,000 D and approximately 2 to 75 unit per milliliter heparin of a molecular weight greater than approximately 3 KD;

thereafter draining excess liquid from the soft tissue so treated;

thereafter immersing the soft tissue in an aqueous heparin solution of approximately 20 to 500 unit per milliliter concentration, and thereafter freezing the tissue and lyophilizing the tissue to dryness.

The features of the present invention can be best understood together with further objects and advantages by reference to the following detailed description of specific examples and embodiments.

DESCRIPTION OF THE PREFERRED EMBODIMENTS

The following specification sets forth the preferred embodiments of the present invention. The embodiments of the invention disclosed herein are the best modes contemplated by the inventors for carrying out their invention, although it should be understood that various modifications can be accomplished within the parameters of the present invention.

In accordance with the present invention soft tissue intended for graft in mammals, including humans, is first obtained from a source, such as cadavers. Bovine, ovine, porcine tissue and soft tissue obtained from other animals, such as sheep, serve as examples. Human soft tissue may also be used. Homografts, that is tissues implanted in the same species as the donor, as well as xenografts, that is tissues implanted in species different from the donor, can be prepared in accordance with the present invention. The types of tissues used in accordance with the present invention are generally the same which are normally used in state-of-the-art surgical procedures involving implantations of soft tissues, primarily in humans. Examples of tissues frequently utilized in these procedures are pericardium, aortic and pulmonary roots, tendons, ligaments, skin, peritonium, pleura, mitral and tricuspid valves.

The soft tissue excised from the donor is usually trimmed to remove loose excess or unneeded tissue and fat. Usually the tissue is then kept in saline solution. Thereafter, and in accordance with the present invention, the tissue is treated in a first aqueous solution containing a $C_1$–$C_3$ alcohol in relatively low concentration (approximately 15–35), and thereafter in a second aqueous solution of greater alcohol concentration, in the range of approximately 25 to 75% volume by volume. (All concentrations described in this application are volume by volume, unless specifically stated otherwise.) The purpose of the treatment of the tissue specimen with the first and second solutions is to gradually replace the water content of the specimen with alcohol. Methyl, ethyl and iso-propyl alcohols can be used for this purpose with ethyl alcohol being preferred. Other, non-toxic polar and water miscible organic solvents e.g. acetonitrile, acetone or methyl-ethyl ketone can also be used instead of the above-listed alcohols, and mixtures of alcohols and organic solvents are also suitable for use in the invention. Preferably, the first solution contains approximately 25% ethyl alcohol, the balance being water, and the second solution contains approximately 50% ethyl alcohol, the balance being water.

Those skilled in the art will readily recognize that the foregoing manipulations represent treatment of the tissue specimen with a stepwise increasing gradient of alcohol (or other suitable non-toxic water miscible organic solvent) concentration, until a concentration of at least approximately 25%, preferably approximately 50%, and at most approximately 75% alcohol (or other suitable solvent) concentration is reached. Instead of treating the tissue specimen with the aforesaid concentration gradient in two steps, the specimen could also be treated with the gradient in three or more steps, or even with a continuously increasing gradient until the upper limit of the alcohol (or other suitable solvent) concentration is reached. The treatment with the increasing gradient of alcohol (or other suitable solvent) concentration is conducted at ambient temperature and is best performed by immersing the tissue specimen in the solutions. The timing of the exposure of the tissue specimen to these solutions is not critical and is somewhat dependent on the thickness of the specimen. However sufficient time must be given for the solution to penetrate the specimen. Typically, 30 minutes are sufficient and in the preferred embodiments of the process of the invention the tissue specimen are kept for approximately 30 minutes in each of the first and second alcohol solutions.

After immersion (treatment) in the above-described alcohol solutions, the tissue specimen is immersed (treated) in a third solution that contains approximately 10 to 50% glycerol, approximately 3 to 20% weight by volume polyethylene glycol of a molecular weight in the range of 6,000 D to 15,000 D and approximately 2 to 75 unit per milliliter heparin of a molecular weight greater than approximately 3 KD. Preferably, the third solution contains approximately 20% glycerol, approximately 5% (weight by volume) polyethylene glycol that has a molecular weight of approximately 8,000 D and approximately 50 unit per milliliter heparin. Instead of glycerol, a low molecular weight (<1000 D) polyethylene glycol can be included in the third solution. The duration of immersion in the third solution is also not critical, approximately 30 minutes are sufficient for very thin tissues such as ovine, porcine, bovine or human pericardium, but for thicker tissues longer times of exposure, such as 6 hours, or preferably 12 hours are convenient and preferred.

After treatment with the third solution, the tissue specimen is removed therefrom and excess liquid is allowed to drain from the specimen. The specimen is then briefly (for seconds as in a quick dip) immersed in, or is otherwise treated with aqueous heparin solution of approximately 20 to 500 unit/ml concentration, and preferably of approximately 250 ml/unit concentration, then the heparin solution is allowed to drain off. Thereafter, the specimen is frozen in a manner usual in the art for freezing specimens prior to lyophilization. Those skilled in the art understand that freezing is usually conducted in a freezer of ultra-low temperature, that is between approximately −60° C.—−80° C. After freezing, the tissue specimen is lyophilized (dried in vacuo) in a manner known in the art.

Tissue samples processed in accordance with the invention tend to be translucent and have a slight yellowish tint in color. Unlike tissues lyophilized from 100% water or physiological saline solution, the tissues of the invention are pliable, compliant and do not crack or break as a result of physical manipulations.

For use in surgical procedures as an implant, and for most tests conducted in accordance with the present invention to compare the treated tissues with fresh tissues, the lyophilized tissues are first rehydrated in physiological buffered saline. This is done by treating, preferably by immersing, the lyophilized tissue of the invention in physiological buffered saline solution for approximately 5 minutes to one hour. The rehydrated tissues of the invention have an appearance that is practically indistinguishable from the appearance of the fresh tissue. Rehydration is typically conducted at ambient temperature. It can be done, other than in saline, in the patient's own blood, in tissue culture medium, and in low percentage (<10%) ethyl alcohol solution. A preferred method of rehydrating tissue specimen in accordance with the present invention is in buffered saline of pH 7.4.

As noted above, except for testing the tissue specimen of the present invention, rehydration is performed only prior to use of the tissue specimen for implantation. Otherwise the specimen are stored and transported at ambient temperature in a sealed container protected from atmospheric moisture. The lyophilized tissues can be readily sterilized by gas phase sterilization methods, and can also be implanted without first being rehydrated.

The tissue specimen of the invention do not contain viable cells, but tests described below demonstrated that after rehydration the tissue specimen are not cytotoxic and are compatible for host endothelial cells to attach and proliferate on them. This attachment and proliferation of host cells and lack of cytotoxicity are important for long term survival of most implants. The tissues of the invention are hemocompatible and resistant to platelet aggregation and thrombus formation. Tests, described below, also demonstrated that the collagen fibers of the native tissue have remained substantially intact during the steps of the process of the invention, and are substantially intact in the rehydrated tissue.

Specific Examples and Description of Tests (a) Preparation of Lyophilized Bovine or Ovine Pericardium Fresh bovine and ovine pericardium was cut into strips and squares were dissected to remove loose tissues and fat. The tissues were immediately placed in aqueous 25% ethyl alcohol solution for 30 minutes. The aqueous 25% ethyl alcohol solution was replaced by aqueous 50% ethyl alcohol solution for another 30 minutes. The second (50% ethyl alcohol) solution was then replaced for approximately 16 hours by a third solution containing 20% glycerol, 5% weight by volume polyethylene glycol (MW 8,000) and 50 unit/ml heparin (molecular weight>3 KD). The tissues were carefully removed from the third solution, excess liquid was allowed to drain from the tissues and the tissues were dipped in a heparin solution of 250 unit/ml for a few seconds, prior to freezing the tissues at −70° C. The completely frozen tissues were lyophilized to dryness.

The lyophilized bovine or ovine pericardium tissues obtained above had a translucent appearance and a slight yellowish tint. They were pliable and did not crack or break by physical manipulations. They could be rehydrated by immersion in physiological buffered saline for approximately 5 minutes at ambient temperature. After rehydration, the tissues were indistinguishable in appearance from the native fresh tissues.

Human fibroblasts and umbilical cord vein endothelial cells were cultured on the rehydrated pericardium tissues to study their biocompatibility. Round discs of the tissues were cut to fit the bottom of the wells of a 24 well culture plate. Plastic rings were placed on top of the tissues to hold the tissues down and to ensure a good seal at the edge of the tissues. Cells were seeded on the tissues in normal culture media for one week. At the end of the incubation period, tissues were recovered and cut into different portions for histology studies. Histological examination of the cross-section of the tissues showed a thin layer of endothelial cells adhering to the surface of the tissues. Cells on the tissues were also released by trypsin and counted. These results showed that the rehydrated tissues are not cytotoxic and are biocompatible for host cells to attach and proliferate. As is known, attachment and proliferation of endothelial cells and other connective tissue cells on cardiac implants is essential for the long term survival of the implant.

The integrity of the collagen fibers in the treated tissues was examined by melting temperature measurements. For these, tissues were heated in phosphate buffered saline from 37° C. until they shrunk. The shrinkage temperature of the fresh native tissues and of the lyophilized and rehydrated tissues in accordance with the present invention was approximately the same, at approximately 63+1° C., indicating that the collagen fibers remained intact throughout the lyophilization and rehydration process.

(b) Preparation of Lyophilized Sheep Aortic and Pulmonary Roots

Aortic and pulmonary roots of donor sheep were also treated with the aqueous 25% ethyl alcohol, aqueous 50% ethyl alcohol, aqueous 20% glycerol 5% polyethylene glycol, and subsequent heparin solution and lyophilized, as described above for the bovine and ovine pericardium.

The treated roots were rehydrated and implanted as homografts in the descending aorta of host sheep. Our results show that after 100 days of implantation, the valves were competent and the roots do not appear different from the un-implanted native tissues. The hundred-day explant was free of fibrin deposition and free of host tissue reaction. The leaflets of the valve appeared intact and indistinguishable from the unimplanted valve by both gross observation and histological examination.

What is claimed is:

1. A pliable uncrosslinked soft tissue specimen which has been prepared in a process comprising the steps of:
   (1) treating natural soft tissue obtained from a donor with:
      (a) liquid compositions of gradually increasing concentrations of a polar organic solvent or solvents, until the last of said liquid compositions contains at least approximately 25% and at most 75% by volume of said solvent, or mixture of solvents, the balance being water, the solvent being selected from a group consisting of aliphatic alcohols having 1 to 3 carbons and other water miscible polar organic solvents;
      (b) thereafter with a second liquid composition of aqueous glycerol or of low molecular weight polyethylene glycol having a molecular weight less than approximately 1000 D, containing the glycerol or the low molecular weight polyethylene glycol, or mixtures thereof being in a concentration range of approximately 10 to 50% by volume, said second liquid composition also containing approximately 3–20% weight by volume polyethylene glycol of a molecular weight in the range of 6,000 D to 15,000 D and approximately 2 to 75 units per milliliter heparin of a molecular weight greater than approximately 3 KD;

(2) thereafter briefly immersing the soft tissue in an aqueous heparin solution, and (3) thereafter freezing the tissue and lyophilizing the tissue to dryness.

2. The pliable soft tissue specimen in accordance with claim 1 wherein in the process of preparing the specimen the polar organic solvents are selected from the group consisting of methyl alcohol, ethyl alcohol, iso-propyl alcohol, acetonitrile, acetone and methyl ethyl ketone.

3. The pliable soft tissue specimen in accordance with claim 1 wherein in the process of preparing the specimen the natural soft tissue obtained from the donor is treated with liquid compositions of gradually increasing concentrations of a polar organic solvent or solvents, until the last of said liquid compositions contains at least approximately 50% by volume of said solvent, or mixture of solvents.

4. The pliable soft tissue specimen in accordance with claim 3 wherein in the process of preparing the specimen the polar organic solvent is ethyl alcohol.

5. The pliable soft tissue specimen in accordance with claim 1 wherein in the process of preparing the specimen the second liquid composition contains approximately 18% by volume of glycerol.

6. The pliable soft tissue specimen in accordance with claim 1 wherein in the process of preparing the specimen the natural soft tissue is treated in succession with two liquid compositions of a polar organic solvent or solvents, the first of said compositions containing approximately 15 to 35% by volume of the solvent or solvents, the second of said composition containing approximately 25 to 75% by volume of the solvent or solvents.

7. The pliable soft tissue specimen in accordance with claim 1 wherein the process of preparing the specimen further comprises the step of rehydrating the lyophilized tissue specimen.

8. A pliable uncrosslinked soft tissue specimen, for eventual implantation in a mammal to replace or augment native tissue, which has been prepared in a process comprising the steps of:

(1) treating natural soft mammalian tissue obtained from a donor with:

(a) liquid compositions of gradually increasing concentrations of an aliphatic alcohol or mixture of aliphatic alcohols having 1 to 3 carbon atoms, until the last of said liquid compositions contains at least approximately 25% by volume of said alcohol or mixture of alcohols, the balance being water;

(b) thereafter with a second liquid composition of aqueous glycerol containing the glycerol in a concentration range of approximately 10 to 50% by volume, said second liquid composition also containing approximately 3–20% weight by volume polyethylene glycol of a molecular weight in the range of 6,000 D to 15,000 D and approximately 2 to 75 units per milliliter heparin of a molecular weight greater than approximately 3 KD;

(2) thereafter briefly immersing the soft tissue in an aqueous heparin solution of approximately 20 to 500 units per milliliter concentration, and (3) thereafter freezing the tissue and lyophilizing the tissue to dryness.

9. The soft tissue specimen in accordance with claim 8 wherein in the process of preparing the specimen the aliphatic alcohol is ethyl alcohol.

10. The soft tissue specimen in accordance with claim 9 wherein in the process of preparing the specimen the natural soft tissue is treated with said compositions containing ethyl alcohol, until the last of said compositions contains at least approximately 50% by volume ethyl alcohol.

11. The soft tissue specimen in accordance with claim 10 wherein in the process of preparing the specimen the concentration of glycerol in the second liquid composition is approximately 20% by volume.

12. The soft tissue specimen in accordance with claim 11 wherein in the process of preparing the specimen the concentration of polyethylene glycol in the second liquid composition is approximately 5% weight by volume and the molecular weight of said polyethylene glycol is approximately 8,000 D.

13. The soft tissue specimen in accordance with claim 12 wherein in the process of preparing the specimen the natural soft tissue is treated in succession with two liquid compositions of ethyl alcohol, the first of said compositions containing approximately 15 to 35% by volume of ethyl alcohol, the second of said composition containing approximately 25 to 75% by volume of ethyl alcohol.

14. The soft tissue specimen in accordance with claim 8 wherein the process of preparing the specimen further comprises the step of rehydrating the lyophilized tissue specimen.

15. The soft tissue specimen in accordance with claim 12 wherein in the process of preparing the specimen the natural soft mammalian tissue is selected from the group consisting of pericardium, pleura, peritoneum from aortic valve, pulmonary valve, mitral valve, tricuspid valve, tendon and skin.

16. A pliable soft tissue specimen which has been prepared in a process comprising the steps of:

(1) treating natural soft tissue obtained from a donor with:

(a) liquid compositions of gradually increasing concentrations of a polar organic solvent or solvents, until the last of said liquid compositions contains at least approximately 25% and at most 75% by volume of said solvent, or mixture of solvents, the balance being water, the solvent being selected from a group consisting of aliphatic alcohols having 1 to 3 carbons and other water miscible polar organic solvents;

(b) thereafter with a second liquid composition of aqueous glycerol or of low molecular weight polyethylene glycol having a molecular weight less than approximately 1000 D, containing the glycerol or the low molecular weight polyethylene glycol, or mixtures thereof being in a concentration range of approximately 10 to 50% by volume, said second liquid composition also containing approximately 3–20% weight by volume polyethylene glycol of a molecular weight in the range of 6,000 D to 15,000 D and approximately 2 to 75 units per milliliter heparin of a molecular weight greater than approximately 3 KD;

(2) thereafter briefly immersing the soft tissue in an aqueous heparin solution, and (3) thereafter freezing the tissue and lyophilizing the tissue to dryness.

17. The pliable soft tissue specimen in accordance with claim 16 wherein in the process of preparing the specimen the polar organic solvents are selected from the group consisting of methyl alcohol, ethyl alcohol, iso-propyl alcohol, acetonitrile, acetone and methyl ethyl ketone.

18. The pliable soft tissue specimen in accordance with claim 16 wherein in the process of preparing the specimen the natural soft tissue obtained from the donor is treated with liquid compositions of gradually increasing concentrations of a polar organic solvent or solvents, until the last of said liquid compositions contains at least approximately 50% by volume of said solvent, or mixture of solvents.

19. The pliable soft tissue specimen in accordance with claim 18 wherein in the process of preparing the specimen the polar organic solvent is ethyl alcohol.

20. The pliable soft tissue specimen in accordance with claim 16 wherein in the process of preparing the specimen the second liquid composition contains approximately 18% by volume of glycerol.

21. The pliable soft tissue specimen in accordance with claim 16 wherein in the process of preparing the specimen the natural soft tissue is treated in succession with two liquid compositions of a polar organic solvent or solvents, the first of said compositions containing approximately 15 to 35% by volume of the solvent or solvents, the second of said composition containing approximately 25 to 75% by volume of the solvent or solvents.

22. The pliable soft tissue specimen in accordance with claim 16 wherein the process of preparing the specimen further comprises the step of rehydrating the lyophilized tissue specimen.

23. A pliable soft tissue specimen, for eventual implantation in a mammal to replace or augment native tissue, which has been prepared in a process comprising the steps of:
  (1) treating natural soft mammalian tissue obtained from a donor with:
    (a) liquid compositions of gradually increasing concentrations of an aliphatic alcohol or mixture of aliphatic alcohols having 1 to 3 carbon atoms, until the last of said liquid compositions contains at least approximately 25% by volume of said alcohol or mixture of alcohols, the balance being water;
    (b) thereafter with a second liquid composition of aqueous glycerol containing the glycerol in a concentration range of approximately 10 to 50% by volume, said second liquid composition also containing approximately 3–20% weight by volume polyethylene glycol of a molecular weight in the range of 6,000 D to 15,000 D and approximately 2 to 75 units per milliliter heparin of a molecular weight greater than approximately 3 KD;
  (2) thereafter briefly immersing the soft tissue in an aqueous heparin solution of approximately 20 to 500 unit per milliliter concentration, and
  (3) thereafter freezing the tissue and lyophilizing the tissue to dryness.

24. The soft tissue specimen in accordance with claim 23 wherein in the process of preparing the specimen the aliphatic alcohol is ethyl alcohol.

25. The soft tissue specimen in accordance with claim 24 wherein in the process of preparing the specimen the natural soft tissue is treated with said compositions containing ethyl alcohol, until the last of said compositions contains at least approximately 50% by volume ethyl alcohol.

26. The soft tissue specimen in accordance with claim 25 wherein in the process of preparing the specimen the concentration of glycerol in the second liquid composition is approximately 20% by volume.

27. The soft tissue specimen in accordance with claim 26 wherein in the process of preparing the specimen the concentration of polyethylene glycol in the second liquid composition is approximately 5% weight by volume and the molecular weight of said polyethylene glycol is approximately 8,000 D.

28. The soft tissue specimen in accordance with claim 27 wherein in the process of preparing the specimen the natural soft tissue is treated in succession with two liquid compositions of ethyl alcohol, the first of said compositions containing approximately 15 to 35% by volume of ethyl alcohol, the second of said composition containing approximately 25 to 75% by volume of ethyl alcohol.

29. The soft tissue specimen in accordance with claim 23 wherein the process of preparing the specimen further comprises the step of rehydrating the lyophilized tissue specimen.

30. The soft tissue specimen in accordance with claim 23 wherein in the process of preparing the specimen the natural soft mammalian tissue is selected from the group consisting of pericardium, pleura, peritonium from aortic valve, peritonium from pulmonary valve, peritonium from mitral valve, peritonium from tricuspid valve, tendon and skin.

* * * * *